United States Patent [19]

Vogel et al.

[11] Patent Number: 5,244,671

[45] Date of Patent: Sep. 14, 1993

[54] DERIVATIVES OF PORPHYCENE FOR PHOTODYNAMIC THERAPY OF CANCER

[75] Inventors: Emanuel Vogel, Cologne; Peter A. Koch, Frankfurt; Afssaneh Rahbar, Frechen-Königsdorf, all of Fed. Rep. of Germany; Alexander D. Cross, Atherton, Calif.

[73] Assignee: Cytopharm, Inc., Menlo Park, Calif.

[21] Appl. No.: 647,474

[22] Filed: Jan. 29, 1991

[51] Int. Cl.$^5$ .................. A61K 37/22; A61K 31/40
[52] U.S. Cl. ................................. 424/450; 514/410
[58] Field of Search ............... 514/422, 410, 4, 31; 424/450

[56] References Cited

U.S. PATENT DOCUMENTS

| | | | |
|---|---|---|---|
| 3,592,930 | 7/1971 | Katz et al. | 424/243 |
| 3,989,815 | 11/1976 | Rajadhyaksha | 424/60 |
| 3,989,816 | 11/1976 | Rajadhysksha | 424/60 |
| 3,991,203 | 11/1976 | Rajadhyaksha | 424/274 |
| 4,017,615 | 4/1977 | Shastri et al. | 424/241 |
| 4,411,893 | 10/1983 | Johnson et al. | 424/181 |
| 4,448,765 | 5/1984 | Ash et al. | 424/14 |
| 4,721,612 | 1/1988 | Janoff et al. | 424/1.1 |
| 4,837,028 | 6/1989 | Allen | 424/450 |
| 4,913,907 | 4/1990 | Jori et al. | 424/241 |
| 4,996,312 | 2/1991 | Sakata et al. | 540/145 |

FOREIGN PATENT DOCUMENTS 9006748  6/1990  World Int. Prop. O.

OTHER PUBLICATIONS

Will et al "Isocorroles . . ." Chem Abst 114:61799, Feb. 18, 1991, of *Angew Chem* 102:1434–7, 1990.
*Tetrahedron Letters* No. 50, (1975), pp. 4467–4470, "A Convenient Synthesis of Acetylenes: Catalytic Substitutions of Acetylenic . . ." Sonogashira et al.
*J. Org. Chem.*, (1976), vol. 41, pp. 2826–2835, "Pyrrole Chemistry. the Cyanovinyl Aldehyde Protecting Groups", Paine et al.
*J. Org. Chem.*, (1988), vol. 53, pp. 2787–2795, "5–Unsubstituted 2–Pyrrolecarboxaldehydes for Porphyrin Synthesis and the Cyanovinyl . . ." Paine et al.
*Angew. Chem. Int. Ed. Engl.*, (1988), vol. 27, pp. 1170–1172, "Biomimentic Synthesis of an Octabinylogous Porphyrin with an Aromatic . . ." Knubel et al.
*Angew. Chem.*, (1988), vol. 100, pp. 1203, 1204 & 1211, "Biomimetische Synthese Eines Octabinylogen Porphyrins mit Aromatischem . . ." Knubel et al.
*Angew. Chem. Int. Ed. Engl.*, (1986), 25, pp. 1100–1101, "Synthesis of a Fourfold Enlarged Porphyrin with an Extremely Large, Diamagnetic Ring . . ." Gosmann et al.
*Angew. Chem.*, (1986), vol. 98, pp. 1107–1108, "Synthese Eines Vierfach Aufgeweiteten Porphyrins mit Extrem Hohem Diamagnetischem . . ." Gosmann et al.
*J. Org. Chem.*, (1987), 52, pp. 710–711, "Synthesis of a [1,5,1,5]Platyrin, a 26–Electron Tetrapyrrolic Annulene", Schlessinger et al.
*J. Am. Chem. Soc*, (1988), 110, pp. 5586–5588, "An 'Expanded Porphyrin': The Synthesis and Structure of a New Aromatic Pentadentate . . .", Sessler et al.
*Tetrahedron Letters No.* 44, (1978), pp. 4225–4228, "The Synthesis of a 22–Electron Tetrapyrrolic Macrocycle. [1.3.1.3]Platyrin", Berger et al.
*Chemistry Letters*, (1973), pp. 1041–1044, "Reductive Coupling of Carbonyl Compounds to Pinacols and Olefins by Using . . ." Mukaiyama et al.
*J. Am. Chem. Soc.*, (1974), 96, pp. 4708–4709, "A New Method for the Reductive Coupling of Carbonyls to Olefins. Synthesis of –Carotene", McMurry et al.
*Organic Synthesis*, pp. 880–883, "Palladium Catalyst for Partial Reduction of Acetylenes", Lindlar et al (1962).
*Cancer Research*, (1978), 38, pp. 2628–2633, "Phtoradiation Therapy for the Treatment of Malignant Tumors", Dougherty et al.
*Chemical Abstracts*, (1989), No. 24, 111:224097K, "Electrochemical, Theoretical, and ESR Characterizations of Porphycenes", Renner et al.

*Primary Examiner*—Frederick E. Waddell
*Assistant Examiner*—Gregory Hook
*Attorney, Agent, or Firm*—Oblon, Spivak, McClelland, Maier & Neustadt

[57] ABSTRACT

New porphycene compounds useful as photodynamic therapy agents. The porphycene compounds have an active group capable of binding to proteins and peptides and facilitating decomposition of the porphycenes following therapy.

19 Claims, No Drawings

DERIVATIVES OF PORPHYCENE FOR PHOTODYNAMIC THERAPY OF CANCER

BACKGROUND OF THE INVENTION

1. Field of the Invention

The invention relates to novel porphycene compounds and pharmaceutical compositions containing these compounds which are useful for therapeutic treatment.

2. Discussion of the Background

During the past few years there has developed a widespread recognition that modern, though sophisticated, cancer diagnosis and treatments have served neither to reduce overall the number of case of reported cancers in the U.S.A. nor, save the notable cases, the death rate. This is a disheartening result for the billions of dollars invested in conquering the disease. Moreover, surgery, radiotherapy and chemotherapy are all associated with major debilitating side effects such as trauma, severe immunosuppression or toxicity which are not easily surmounted by patients already compromised by ill-health.

Early work in the 1970's followed by rapidly expanding studies in the 1980's, has shown that photodynamic therapy (PDT) offers a viable, less toxic and generally less painful avenue to treatment of cancer. Not all cancers are candidates for PDT. However, intractable tumor masses (solid tumors, frequently characterized by poorly developed vascular system), sometimes inoperable, and with no good track record for treatment by established therapeutic procedures, appear to be targets for PDT.

Dougherty et al (Cancer Res., 1978, 38, 2628) pioneered the field with infusion of photoactivatable dyes, followed by appropriate long wavelength radiation of the tumors (600+ nm) to generate a lethal short-lived species of oxygen which destroyed the neoplastic cells. Early experiments utilized a mixture termed haematoporphyrin derivative (HPD). The deficiencies of HPD, especially prolonged phototoxicity caused by retained HPD components in human skin led to its displacement by a purified fraction termed dihaematoporphyrin ether (DHE) which, although yielding improvements over HPD, nevertheless still suffered certain practical limitations. Relatively weak absorption in the wavelength range 600-700 nm, retention in dermal cells (potentially leading to phototoxicity) and uncertain chemical constitution are all known negative features. The great majority of the earlier PDT agents studied have been derived from natural sources (porphyrins, chlorins, purpurins, etc.) or from known chemicals originating in the dyestuffs industry (e.g., cyanine dyes).

As the deficiencies of these earlier agents have become apparent, it also becomes possible to define activity parameters for improved chemically pure photoactivatable dyes for PDT therapy, available by chemical synthesis. Moreover, the products of synthesis lend themselves more readily to further chemical structural manipulation than do the naturally-occurring starting materials which can be expensive and bear chemically sensitive constituents. The synthesis of the novel porphycene macrocycle embracing four pyrrole rings, has been described by Vogel and coworkers. Alkylated porphycenes have also been prepared (R=Me, Et, n-Pr, n-octyl, phenyl) and the photochemical properties determined. The suitability of these compounds for PDT was noted and confirmed in animal studies (Cancer Letters, 1989, 44, 1).

Pyrrole-containing ring systems larger than porphycene have also been prepared and evaluated as photosensitizers. Sessler et al have prepared and studied texaphyrin (J. Am. Chem. Soc., 1988, 110, 5586) and Woodward et al and Johnson et al have prepared and investigated sapphyrin ring systems. Additionally, the platyrin system has been studied by LeGoff (Tetrahedron, Lett., 1978, 4225; J. Org. Chem., 1987, 710) and vinylogous porphyrins have been studied by Franck (Angew. Chem., 1986, 98, 1107; Angew. Chem. Int. Ed. Eng., 1986, 25, 1100; Angew. Chem., 1988, 100, 1203; Angew. Chem. Int. Ed. Eng., 1988, 27, 1170).

A need continues to exist, therefore, for new compounds for use in PDT therapy, which compounds are easily available, have low intrinsic toxicity, are efficient photosensitizers for singlet oxygen production, have selective uptake in rapidly proliferating cells, are rapidly or at least moderately rapidly degraded and eliminated from the tissues after administration and which are available as chemically pure and stable compounds easily subject to synthetic modification.

SUMMARY OF THE INVENTION

Accordingly, one object of the present invention is to provide new and effective compounds for use in photodynamic therapy whose properties and characteristics approach the ideal characteristics of PDT dyes listed above.

This and other objects which will become apparent from the following specification have now been achieved with the porphycene compounds of the present invention, which possess both value as PDT agents themselves and also afford great flexibility for the preparation of further derivatives. The present compounds have utility as PDT dyes for use in cancer therapy and dermatological diseases.

DETAILED DESCRIPTION OF THE PREFERRED EMBODIMENTS

The present porphycene compounds are aromatic and exhibit improved absorption and singlet oxygen photosensitization characteristics. Additionally, the compounds of the present invention contain a substituent capable of attachment to selected proteins. The active group serves as a "handle" for attachment of the protein. Further, the active group accelerates metabolism of the porphycene dye thereby destroying in vivo the light absorbing tetrapyrrole porphycene chromophore to generate non-photoactivatable metabolites which are photochemically innocuous and unable to cause post-PDT phototoxicity. Compounds of the present invention are therefore superior to simple alkylated porphycenes with regard to rapid clearance from the body after administration.

The development of PDT agents suitable for treating dermatological disease, such as psoriasis, requires that the photoactivatable porphycene clear fairly rapidly from dermal tissue after topical or systemic administration and irradiation. Since light of wavelength 600-650 nm loses most of its energy after penetrating only about 1 cm into human tissue, this is more appropriate than deeper penetrating longer wavelengths for dye activation in these applications. Tumors which are close to surfaces where light can be applied are also targets for PDT dyes absorbing at these shorter (600-650 nm) wavelengths. Since dye transport, mobility, binding by cell receptors, etc., are all related to chemical structure, and especially to the lipophilicity or hydrophilicity of the dye, it is clearly beneficial to have available a primary chemical structure which can be subject to extensive chemical structural manipulation.

The porphycene compounds of the present invention have structures I and II shown below:

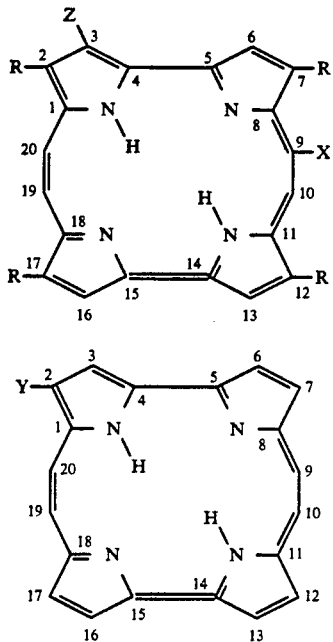

where in structure (I),

R is H, alkyl, aralkyl, aryl or substituted alkyl, aralkyl and aryl, when Z is H, X is $NO_2$, $-NR_1R_2$, where $R_1$ and $R_2$ each independently may be the same groups identified for R above, $-NH-CO-R_3$ where $R_3$ is R, an amino acid, a peptide, or a protein, $-OR$, $-OCOR$, $-O-SO_2R$, $-O-$(amino acid), $-O-$(glycoside), $-O-$(peptide), $-O-$(protein) or halogen (Cl, Br) and when X is H and R is as above, Z is chlorine, bromine or iodine; and where in structure (II), Y is chlorine or bromine; and salts thereof.

The term "alkyl" and "aralkyl" as used herein, include both straight and branched-chain saturated aliphatic groups. Preferred alkyl groups for R contain from 1 to 10 carbon atoms in either the alkyl or aralkyl groups. The term "aryl" and "aralkyl" include carbocyclic aromatic ring substituents as well as heterocyclic aromatic substituents. The heteroaromatic ring may contain one or more nitrogen, oxygen or sulfur heteroatoms. Preferably, the heteroaromatic ring contains 1–3 heteroatoms. The aryl and aralkyl groups preferably contain 4–10 carbons atoms in the aromatic moiety.

Particularly preferred alkyl groups are those containing 1–6 carbon atoms, optionally substituted with halogen, amino or nitro groups. Preferred aryl groups are phenyl and phenyl substituted with halogen, $C_{1-6}$ alkyl, nitro, or amino groups. Preferred aralkyl groups are $C_{1-6}$ alkyl-phenyl groups, optionally substituted on the phenyl ring or alkyl portion of the aralkyl group with halogen, $C_{1-6}$ alkyl, nitro, or amino groups.

Preferred ethers, esters and porphycene sulfonates (X is $-OR$, $-OCOR$, and $-OSO_2R$) are the $C_{1-10}$ alkyl, aralkyl and phenyl ether, ester and sulfonate compounds (R is $C_{1-10}$ alkyl, aralkyl or phenyl). If desired, the $C_{1-10}$ alkyl, aralkyl and phenyl groups may be further substituted with additional $C_{1-6}$ alkyl, halogen, nitro, or amino substituents.

The present invention also includes porphycene compounds in which the ether group $-OR$ forms part of an acetal or ketal group. Acetal and ketal groups can be prepared by conventional synthesis from the hydroxyporphycene. For example, the acid-catalyzed addition of a vinyl ether, such as dihydropyran, methyl 2-propenyl ether or ethyl vinyl ether, to a hydroxyporphycene yields the corresponding tetrahydropyranyl, 2-methoxyisopropyl and 1-ethoxyethyl groups, respectively. Particularly preferred are tetrahydropyranyl (THP) ethers.

When the compound contains an amino acid, a peptide or a protein, the amino acid is generally bonded to the compound by means of an amide or ester linkage. For example, an amino acid may be bonded through a carbonyl group on the porphycene by means of the alpha-amino group (or other amino group present in the amino acid) to form an amide linkage. When bonded to the porphycene by means of an ester linkage, the alpha-carboxyl group (or other carboxyl group present in the amino acid) may be used to form the ester linkage through a hydroxyl group on the porphycene. Suitable amino acids include the 20 naturally occurring amino acids in both the R and S forms as well as nonnaturally occurring synthetic amino acids. Peptides which may be bound to the porphycene ring structure generally contain from 2–10 amino acids, although a complete protein may be bound if desired.

In the porphycene glycosides of the present invention, the sugar moiety, which may consist of a single sugar, either in the open or cyclic form, an oligosaccharide or a polysaccharide, may be attached to the porphycene ring system by means of a conventional glycoside bond. Any of the common monosaccharide sugars, such as glucose, galactose, fructose, mannose, etc. and oligosaccharides thereof may be used to prepare the porphycene glycosides of the present invention. Glycosides are prepared by conventional chemistry in which the porphycene ring structure is substituted with a glycoside moiety (see Scheme 1).

Compounds having utility in PDT, have been prepared bearing substituents on the porphycene ring structure at the 2-, 3- and 9-positions. In these 9-substituted porphycene structures, there is therefore enormous latitude for classic organic chemical molecular variation, applying a whole range of well-known reactions. The 3- and 9- substituents may be introduced as described below, for porphycenes bearing many different substituents at the 2-, 7-, 12- and 17-positions.

The compounds of the present invention can be prepared by the application of known organic synthetic chemistry reactions. Porphycene itself can be synthesized by a McMurry coupling reaction and may serve as the starting material for porphycenes having structure II. Porphycene can be prepared by reacting pyrrole with phosphorus oxychloride and 2-pyrrolidone followed by dehydrogenation (Pd/C, heat) of the product to form a bi-pyrrole. Acylation of the bi-pyrrole product using phosphorus oxychloride and an acylating agent ($RCON(CH_3)_2$ for example) yields the di-acyl compound which can be coupled reductively to form the porphycene ring structure using a titanium reagent ($TiCl_4/Zn$). Modifications of this general scheme allow one to prepare not only the parent porphycene ring structure but also porphycenes bearing substituents at the 2-, 7-, 12- and 17-positions (structure I) by using appropriately substituted pyrroles.

These porphycenes, which bear a substituent in the ring system, are generally obtained by electrophilic substitution reactions. For example, the nitro, bromo, iodo, amino and hydroxy derivatives can be prepared using the substrates and reagents shown in Table 1 below and illustrated in Scheme 1. Although only porphycene is shown in Scheme 1 and only tetrapropyl porphycene in Table 1, obviously, other porphycene bearing different alkyl, aralkyl and aryl substituents may also be used in the reactions shown.

trast to the more lipophilic porphycenes lacking such substituents. Lipophilic and hydrophilic porphycenes concentrate selectively at different sites in a tumor. Derivatives such as sulphonate salts are also important since, cationic and anionic dyes concentrate in different areas of the tumor. Porphycenes covalently bound through peptide linkages to peptides or proteins provide PDT agents with valuable specific transport and binding selectively characteristics.

By conventional chemistry the amino porphycenes are converted to alkyl, alicyclic, aralkyl or aromatic secondary and tertiary amines or to amides. The $NH_2$ substituent may also be converted to a diazonium salt

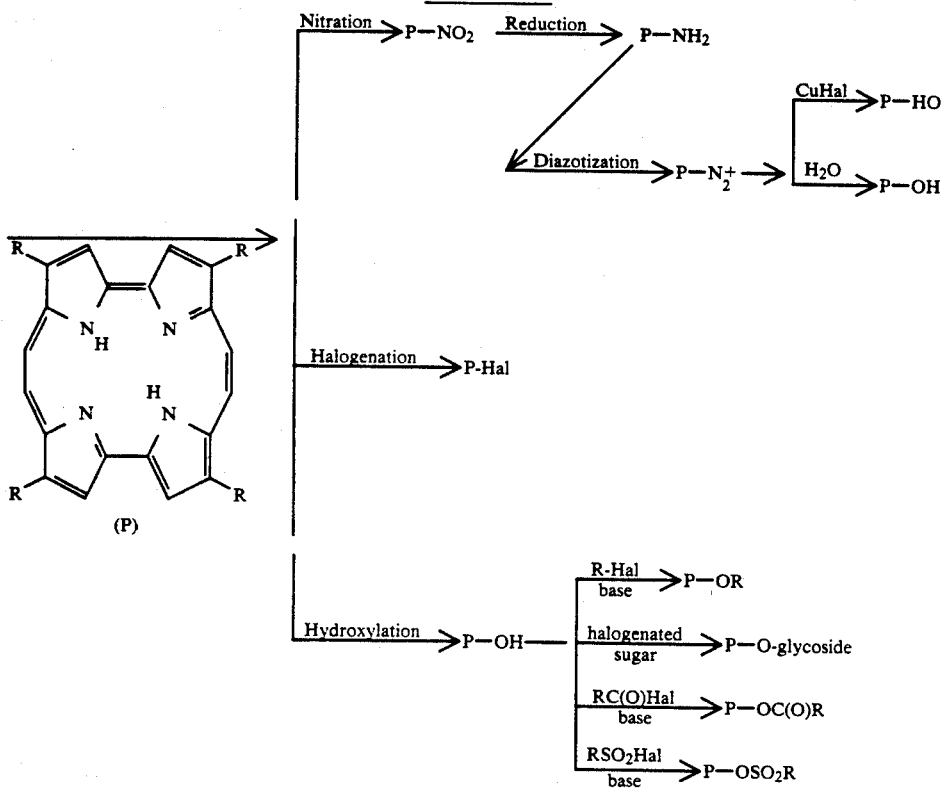

TABLE 1

| Substrate | Reagent | Product |
|---|---|---|
| 2,7,12,17-tetrapropylporphycene | elementary bromine | 3-bromo-2,7,12,17-tetrapropylporphycene |
| 2,7,12,17-tetrapropylporphycene | elementary iodine | 3-iodo-2,7,12,17-tetrapropylporphycene |
| 2,7,12,17-tetrapropylporphycene | silver nitrate | 9-nitro-2,7-12,17-tetrapropylporphycene |
| 2,7,12,17-tetrapropylporphycene | a) silver nitrate b) $Na_2S_2O_4$ | 9-Amino-2,7,12,17-tetrapropylporphycene |
| 2,7,12,17-tetrapropylporphycene | a) lead tetraacetate b) hydrolysis with sodium hydroxide | 9-hydroxy-2,7,12,17-tetrapropylporphycene |

By conventional chemistry the hydroxy porphycenes (alcohols) are convertible to a wide range of aliphatic and aromatic ethers, bearing one or more substituents on the alkyl group or aromatic groups. Hydroxyl derivatives include esters, amino acids, peptides, proteins, sugars, sulfonic acid esters, etc. Polyhydroxylated derivatives such as glycosides containing mono or polysaccharides are of great utility as PDT agents since the resultant porphycene glycoside is hydrophilic in conand by subsequent displacement reactions halo and related derivatives are obtained. The $NH_2$ group also facilitates easy linkage of the porphycene to peptides and proteins with the accompanying transport and binding benefits described above.

Salts of the porphycene compounds of the present invention include conventional acid addition salts obtained by the addition of HCl, $H_3PO_4$, $H_2SO_4$, HBr, etc. Additionally, salts obtained by reaction with functional groups in R are within the scope of the present invention. Such salts include, for example, salts of carboxylic acid and amino groups present in R. All such pharmaceutically acceptable salts are within the scope of the present invention.

All of the many possible derivatives embrace the intact macrocyclic porphycene chromophore and all are capable of generating singlet oxygen under appropriate irradiation conditions, each constituting therefore a prospective photoactivatable dye for use in PDT.

THERAPEUTIC FORMULATIONS

Therapeutic compositions containing the compounds of the present invention include liposome or microvesicle preparations, dispersions, solutions for parenteral injection, etc., and including topical dermatological preparations.

Parenteral Solutions

The photoactivatable porphycene dyes generally are used with additional solvents and adjuvants to prepare solutions suitable for intravenous injection. A number of solvents and co-solvents that are miscible with water and suitable surfactants can be used to achieve solutions for parenteral use. The most important solvents in this group are ethanol, polyethylene glycols of the liquid series and propylene glycol. A more comprehensive listing includes acetone, dimethyl acetamide, dimethyl formamide, dimethyl sulfoxide, ethanol, glycerin, polyethylene glycol 300, and 400, propylene glycol, sorbitol, polyoxyethylene sorbitan fatty acid esters such as laurate, palmitate, stearate, and oleate, polyoxyethylated vegetable oil, sorbitan monopalmitate, 2-pyrrolidone; n-methyl-2-pyrrolidine; n-ethyl-1-pyrrolidine and tetrahydrofurfuryl alcohol.

Other additives may be necessary to enhance or maintain chemical stability and physiological suitability. Examples are antioxidants, chelating agents, inert gases, buffers and isotonicifiers.

Examples of antioxidants and typical concentration ranges include acetone sodium bisulfite (0.1–0.8%), ascorbic acid (0.05–1.0%), monothioglycerol (0.1–1.0%), potassium metabisulfite (0.05–0.1%), propyl gallate (0.02%), sodium bisulfite (0.01–1.0%), sodium formaldehyde sulfoxylate (0.03–0.1%), sodium metabisulfite (0.02–0.25%), sodium sulfite (0.01–0.1%), sodium thioglycolate (0.05–0.1%).

Examples of chelating/complexing agents and typical concentration ranges include edetate sodium (0.005–0.1%), edetate calcium disodium (0.005%–0.01%), gentisic acid ethanolamide (1.0%–2.0%), niacinamide (1.0%–2.5%), sodium citrate (0.01%–2.5%), citric acid (0.001%–1.0%).

Examples of inert gases are nitrogen and carbon dioxide.

Buffers are used primarily to stabilize a solution against the chemical degradation that might occur if the pH changed appreciably. Buffer systems employed normally have as low a buffer capacity as feasible in order to not disturb significantly the body buffer systems when injected. The buffer range and effect of the buffer on activity must be evaluated. Appropriate adjustment is useful to provide the optimum conditions for pH dependent partition into the target malignant tissues or lesion area.

Examples of such buffer systems include the following acids: acetic, adipic, ascorbic, benzoic, citric, glycine, lactic, tartaric, hydrochloric, phosphoric, sulfuric, and carbonic and bicarbonic; and their corresponding salts such as: potassium, sodium, magnesium, calcium and diethanolamine salts.

Osmoticity is of great importance and hypotonic solutions usually have their tonicity adjusted by the addition of salts such as sodium chloride, potassium chloride, magnesium chloride and calcium chloride and sugars such as dextrose, lactose, mannitol and sorbitol.

When the solution will be dispensed from multiple dose containers, antimicrobial agents in bacteriostatic or fungistatic concentrations must be added. Among the compounds and concentrations most frequently employed are phenylmercuric acid (0.002–0.01%), thimerosal (0.01%), benzethonium chloride (0.01%), benzalkonium chloride (0.01%), phenol or cresol (0.5%), chlorbutanol (0.5%), benzyl alcohol (2.0%), methyl p-hydroxybenzoate (0.18%), and propyl p-hydroxybenzoate (0.02%).

After the solution of the porphycene with its solvents and additives has been compounded, the solution is filtered to remove particulate matter above 2 µm in size and a further step eliminating particulate matter down to 0.24 µm can eliminate microorganisms and accomplish cold sterilization. The solution is filled under aseptic conditions. The final solution can be additionally sterilized in its final container by thermal methods such as autoclaving or non-thermal methods such as ionizing radiation. The process of freeze drying (lyophilization) can be employed to avoid adverse thermal and oxidative decomposition and provide enhanced stability and improved solubility.

The following formula provides an example of the utilization of various solvents and additives such as have been heretofore mentioned in the creation of a suitable parenteral solution of the porphycene. The formula is by way of example only and is not limiting to this invention. Suitable combinations and variations are obvious to those skilled in the art.

| Formula example for 9-amino-2,7,12,17-tetrapropylporphycene parenteral solution 1 mg/ml | |
|---|---|
|  | Grams |
| 9-Amino-2,7,12,17-tetrapropylporphycene | 0.1 |
| Tetrahydrofurfurylalcohol | 40.0 |
| Polysorbate 20 | 1.0 |
| Sodium chloride | 0.9 |
| Citric acid buffer | 0.1 |
| water* enough to make 100 ml | |

*water may be water for injection, bacteriostatic water for injection or sterile water for injection.

Method of Preparation

1. Dissolve porphycene in tetrahydrofurfuryl alcohol and polysorbate 20, using heat and stirring as needed.
2. Dissolve sodium chloride and citrate buffer in water.*
3. Add the water solution slowly with stirring and heat as necessary to the solution.
4. Sterile fill using aseptic conditions and use terminal sterilization as needed.

This solution is suitable for a broad dosage range such as 0.1–10 mg/kg and preferably 0.2–5.0 mg/kg and may be infused as such or added to suitable large volume parenteral solutions such as dextrose, saline, ringers solutions for slower intravenous administration. Suitable solutions are described, for example, in REMINGTON'S PHARMACEUTICAL SCIENCES, 15th Ed., Easton: Mack Publishing Co. incorporated herein by reference.

Topical Formulations

The porphycene compounds of the present invention may be formulated for topical application in penetrating solvents or in the form of a lotion, cream, ointment or gel containing a sufficient amount of the porphycene compound to be effective for PDT therapy.

Suitable penetrating solvents are solvents for the porphycene compound which will enhance percutaneous penetration of the porphycene compound. Solvents which have this property include dimethyl sulfoxide, dimethyl acetamide, dimethyformamide and 1-methyl-2-pyrrolidone and to a lesser extent propylene glycol. DMSO solutions containing 0–30 wt. % water are particularly desirable. Additional solvents include substituted azacycloalkan-2-ones having from 5 to 7 carbons in the cycloalkyl group such a 1-dodecylazacycloheptan-2-one (AZONE) and other azacycloalkan-2-ones such as described in U.S. Pat. No. 3,989,816 incorporated herein by reference and having the structure shown below

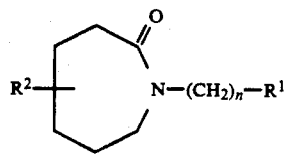

wherein $R^1$ is a straight or branch chain alkyl group having from 1 to 18 carbons or aryl group having from 6 to 10 carbons;

$R^2$ is H or lower alkyl having from 1 to 4 carbons; and n is an integer from 0 to 10.

Also included are N-bis-azacyclopentan-2-onyl alkanes described in U.S. Pat. No. 3,989,815 (hereby incorporated by reference) and having the formula:

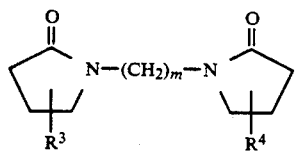

wherein $R^3$ and $R^4$ are each H or a lower alkyl group having from 1 to 4 carbons;

and m is a positive integer of from 1 to 18.

Also included are 1-substituted azacyclopentan-2-ones described in U.S. Pat. No. 3,991,203 (hereby incorporated by reference) and represented by formula:

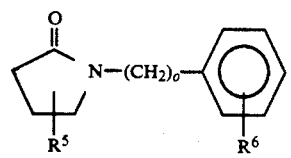

wherein $R^5$ and $R^6$ are each H or lower alkyl having from 1 to 4 carbons; and o is a positive integer from 0 to 10.

Also included are water-soluble tertiary amine oxides described in U.S. Pat. No. 4,411,893 (hereby incorporated by reference) and represented by the following formulas:

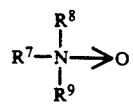

wherein $R^7$, $R^8$ and $R^9$ are each saturated or unsaturated aliphatic radicals optionally containing ether or amide linkages and pendent hydroxyl groups, and the total number of carbon atoms of $R^7$, $R^8$ and $R^9$ does not exceed 28, and

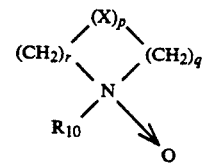

wherein X is —O— or —N($R^{11}$)—;

$R^{10}$ and $R^{11}$ are each saturated or unsaturated aliphatic radicals having from 1 to 18 carbons and optionally containing ether or amide linkages and pendent hydroxyl groups; and p is 0 or 1;

q is 2, 3, or 4; and r is 2 or 3.

The topical formulations contain a sufficient amount of the porphycene compound to be effective in PDT therapy. Generally, concentrations in the range of 0.001 to 5 wt. %, preferably from about 1 to 5 wt. % may be used. Typical lotion and cream formulations are shown below.

| Parts by Weight | Ingredient |
|---|---|
| | LOTION |
| 5 | polyoxylene-40-stearate |
| 3 | sorbitan monostearate |
| 12 | *mixture of lanolin, mineral oil and lanolin alcohol |
| 6 | cetyl alcohol |
| 20 | soybean oil |
| 53.7 | water |
| 0.2 | methyl paraben |
| 0.1 | propyl paraben |
| | CREAM |
| 3 | polyoxyethylene-40-stearate |
| 2.5 | sorbitan monostearate |
| 10 | soybean oil |
| 10 | *mixture of lanolin, mineral oil and lanolin alcohol |
| 1 | cetyl alcohol |
| 73.2 | water |
| 0.2 | methyl paraben |
| 0.1 | propyl paraben |

*AMERCOL BL (Amerchol Corp. Edison, N.J.)

Additional topical formulations which may be used in conjunction with the porphycene compounds of the present invention are disclosed in U.S. Pat. Nos. 3,592,930 and 4,017,615 (hereby incorporated by reference).

Liposome or Microvesicle Preparations

Liposomes and methods of preparing liposomes are known and are described for example in U.S. Pat. No. 4,452,747 and U.S. Pat. No. 4,448,765 incorporated herein by reference. Liposomes are microvesicles which encapsulate a liquid within lipid or polymeric membranes. The porphycene compounds of the present invention may be incorporated into liposome microvesicles and used in this form for both topical and parenteral application. Topical and parenteral (injectable) liposome preparations are known in the art.

U.S. Pat. No. 4,837,028 discloses injectable liposome formulations having enhanced circulation time. The liposomes have a size of about 0.08-0.5 microns, contain at least 50 mole % of a membrane rigidifying component such as sphingomyelin and further contain about 5-15 mole % ganglioside $G_{M1}$. Liposome preparations for encapsulating sparingly soluble pharmaceutical compounds are disclosed in U.S. Pat. No. 4,721,612. The specification of these U.S. patents is incorporated herein by reference.

After administration of a therapeutically effective amount of one or more of the porphycene compounds in the pharmaceutical composition or preparation, to a patient having a treatable condition such as a solid tumor (cancer) or psoriasis, for example, the patient's affected body area is exposed to a therapeutically sufficient amount of light having an appropriate wavelength for absorption by the particular porphycene compound used. Suitable wavelengths are generally from about 600 to about 950 nm, preferably from about 600 to about 750 nm. Irradiation of the accumulated porphycene generates singlet oxygen which is thought to be the actual lethal species responsible for destruction of the neoplastic cells.

Photodynamic therapy using the porphycene compounds of the present invention has a number of advantages. The porphycene compound itself is minimally toxic in the unexcited state. Each porphycene molecule can be repeatedly photoactivated and lead each time to cell-lethal events, that is, the generation of singlet molecular oxygen. The half-life of singlet molecular oxygen is approximately four microseconds in water at room temperature. The target cell is therefore affected without the opportunity for migration of the lethal singlet molecular oxygen to neighboring healthy tissue cells. Singlet oxygen molecules rupture chemical bonds in the cell DNA, target cell wall, or destroy intracellular structures such as mitochondria, resulting in destruction of the target cell. Destruction of target cell tissue commences promptly upon irradiation of the porphycene compounds and ceases abruptly when irradiation is stopped. Photodynamic therapy using the compounds of the present invention is therefore selective and minimally toxic to healthy tissue. Singlet oxygen molecules produced which do not react rapidly with neighboring molecules rapidly decay.

A variety of phototherapy and irradiation methodologies are known to those skilled in the art and can be used with the novel porphycene compounds of the present invention. The time and duration of therapy and repetition of the irradiation treatment can be selected by the therapist (physician or radiologist) according to known photodynamic therapy criteria. The dosage of the porphycene compound may be varied according to the size and location of the target tissues which are to be destroyed and the method of administration. Generally, the dosage will be in the range of 0.1-20 mg of porphycene compound per kilogram of body weight, more preferably in the range of 0.2-5.0 mg/kg.

For cancer therapy irradiation, irradiation generally takes place not less than one hour nor more than four days after administration of the porphycene compound. Usually, phototherapy is begun approximately 10 hours to 24 hours after administration of the photodynamic therapy agent. For dermatological applications, radiation therapy can commence immediately after topical application of the porphycene or up to 12 hours later. Systemic application for treatment of dermatological diseases is followed by radiation usually 15 to 24 hours after systemic administration of the PDT agent. Exposure to nontherapeutic light sources should be avoided immediately following phototherapy to minimize light toxicity. Appropriate draping of the patient can be used to limit the area affected by phototherapy.

Light sources which are appropriate for use are well known in the art and may vary from white light sources with appropriate filters to lasers. As noted above, preferred wavelengths are from 600 to 950 nm, preferably from about 600 to about 750 nm. The total amount of light which is applied to the affected area will vary with the method used and the location of the tumor or topical lesion. Generally, the amount of light is in the range of about 50 to 1000 J-cm$^2$, preferably in the range of 100 to 350 J-cm$^2$.

Having generally described this invention, a further understanding can be obtained by reference to certain specific examples which are provided herein for purposes of illustration only and are not intended to be limiting unless otherwise specified. Procedures which are constructively reduced to practice herein are described in the present tense and procedures which have been carried out in the laboratory are set forth in the past tense.

EXAMPLES

Example 1

9-Nitroporphycene 31 mg (0.1 mmol) of porphycene were dissolved in a mixture of 20 ml of dichloromethane and 10 ml of acetic acid. At 0° C. 0.1 ml of fuming nitric acid were added with stirring. The reaction mixture was quenched after 1 min with cold water, neutralized with saturated NaHCO$_3$ solution and dried over Na$_2$SO$_4$. Chromatography on silicagel with dichloromethane/hexane 1:1 followed by recrystallization from dichloromethane yielded 27 mg (76%) of the nitro compound as small blue needles which decomposed above 300° C.

$^1$H NMR (300 MHz, CDCl$_3$): $\delta = 10.61$, 9.79, 9.69, 9.58, 9.54, 9.51, 9.50, 9.47, 9.24, 9.15, 9.13, 3.72, 3.09; IR (CsI): $\nu = 2926$ cm$^{-1}$, 2850, 1523, 1314, 1158, 1059, 947, 812, 757; UV/VIS (benzene): $\lambda = 348$ sh ($\epsilon = 18400$), 388 (35000), 562 (13000), 603 (11100), 630 (12600).

Example 2

9-Aminoporphycene

To a solution of 18 mg (0.05 mmol) of 9-nitroporphycene in 50 ml of dichloromethane 30 m (0.6 mmol) hydrazine monohydrate and a suspension of 150 mg of Raney nickel in 20 ml of dry methanol were added. The reaction mixture was refluxed for 1 h, filtered, and washed with water. The solution was dried over Na$_2$SO$_4$ and the solvent was evaporated. The residue was purified by chromatography on silicagel with dichloromethane and subsequent recrystallization from dichloromethane The amino compound thus obtained in 37% yield (6 mg) formed violet needles decomposing above 280° C.

¹H NMR (300 MHz, [D₇]DMF): δ=9.56, 9.53, 9.43, 9.34, 9.33, 9.11, 9.02, 8.90, 8.89, 8.88, 8.30, 6.57, 6.56; IR (CsI): $\nu$=3366 cm⁻¹, 3210, 1610, 1561, 1463, 1210, 1039, 921, 802, 746; UV/VIS (benzene): λ=365 sh (ε=59,600), 388 (50,600), 525 sh (2400), 565 (23,400), 677 (20,900), 725 (11,700).

Example 3

2-Bromoporphycene 31 mg (0.1 mmol) of porphycene were dissolved in 60 ml of dry chloroform. 18 mg (0.1 mmol) NBS were added at 10° C. and the reaction mixture was stirred for 10 min. After quenching with water the organic phase was dried over MgSO₄, and the solvent was evaporated. The residue was purified by chromatography on silicagel followed by HPLC (nuoleosil, hexane/dichloromethane 3:1). From the second fraction 9 mg (23%) of the title compound was obtained as violet plates which decomposed above 300° C.

¹H NMR (300 MHz, [D₇]DMF): δ=10.19, 10.16, 10.14, 10.11, 10.06, 9.58, 9.57, 9.47, 3.29, 2.83; ¹³C NMR (75.5 MHz, [D₇]DMF): δ=159.8, 156.8, 150.3, 145.3, 142.3, 141.9, 139.9, 137.3, 134.4, 133.1, 130.6, 129.9, 128.9, 128.8, 126.4, 120.7, 117.9, 115.5; IR (CsI): $\nu$=3108 cm⁻¹, 1554, 1460, 1409, 1247, 1225, 1167, 936, 807, 755; UV/VIS (CH₂Cl₂): λ=363 (ε=137,400), 376 sh (100,000), 565 (35,500), 603 (37,600), 634 (47,700).

Example 4

9-Acetoxyporphycene 270 mg (0.6 mmol) of Pb(OAc)₄ were added to a solution of 31 mg (0.1 mmol) of porphycene in 150 ml of acetic acid. The reaction mixture was then heated to 90° C. for 3h. Thereafter the mixture was quenched with 100 ml of water and extracted with 250 ml of dichloromethane. The organic phase was washed with water, dried over MgSO₄, and the solvent was evaporated. Chromatography of the resulting material on silicagel (dichloromethane/hexane 2:1) and subsequent recrystallization from dichloromethane/hexane led to the isolation of 8 mg (20%) of the title compound in the form of violet plates decomposing above 240° C.

¹H NMR (300 MHz, CDCl₃): δ=9.52, 9.50, 9.48, 9.44, 9.43, 9.41, 9.34, 9.05, 9.04, 9.00, 8.95, 3.01, 2.90, 2.84; ¹³C NMR (75.5 MHz, CDCl₃): δ=172.0, 147.0, 142.8, 141.6, 140.3, 138.3, 137.4, 136.4, 135.5, 133.7, 131.7, 129.7, 129.2, 126.2, 125.4, 125.2, 124.9, 115.3, 115.1, 109.0, 121.6; IR (CsI): $\nu$=3100 cm⁻¹, 2920, 1751, 1367, 1209, 1102, 1057, 951, 756, 651; UV/VIS (CH₂Cl₂): λ=362 (ε=124,000), 375 sh (88,600), 558 (27,600), 601 (24,300), 633 sh (28,200), 641 (32,000).

Example 5

9-Hydroxyporphycene

A solution of 19 mg (0.05 mmol) 9-acetoxyporphycene in 20 ml of dichloromethane was treated with 2 ml of a methanolic solution of KOH (5%) at room temperature. The reaction mixture was stirred for 5 min, washed with water and dried over Na₂SO₄. Chromatography on silicagel (dichloromethane) and subsequent recrystallization from dichloromethane yielded 8 mg (50%) of the hydroxy compound as microcrystalline violet plates; mg.>300° C.

¹H NMR (300 MHz, [D₆]DMSO): δ=12.04, 9.84, 9.79, 9.78, 9.72, 9.65, 9.58, 9.45, 9.36, 9.22, 9.20, 4.45, 4.37; ¹³C NMR (75.5 MHz, [D₆]DMSO): δ=150.2, 147.2, 144.2, 141.3, 138.2, 135.3, 134.8, 134.6, 130.9, 130.8, 129.0, 127.5, 127.4, 125.7, 124.2, 123.9, 116.9, 112.8, 102.9; IR (CsI): $\nu$=3495 cm⁻¹, 3116, 1563, 1465, 1403, 1358, 1199, 1055, 952, 811, 752; UV/VIS (CH₂Cl₂): λ=360 (ε=135,900), 376 (96,700), 557 (42,800), 557 (42,800), 617 sh (23,000), 632 (36,800), 674 (35,700).

Example 6

3-Bromo-2,7,12,17-tetrapropylporphycene 50 mg (0.1 mmol) of 2,7,12,17-tetrapropylporphycene were dissolved in 100 ml of acetic acid. At 0° C. 110 mg (0.2 mmol) of bromine on a polymeric carrier (amberlyst A-26 Br₃-modification) were added. The reaction mixture was stirred for 2 h at the same temperature. After removing the polymer by filtration the solvent was evaporated. The resulting residue was chromatographed on silicagel (hexane/dichloromethane 4:1). Evaporation of the main fraction and recrystallization from hexane led to the isolation of the title compound in 80% yield (48 mg) in the form of blue needles exhibiting a mp. of 199°-201° C.

¹H NMR (300 MHz, CDCl₃): δ=10.11, 9.51, 9.18, 9.08, 3.90, 2.32, 1.98, 1.31; ¹³C NMR (75.5 MHz, CDCl₃): δ=148.5, 147.4, 144.9, 144.7, 143.5, 142.4, 139.0, 138.3, 137.8, 133.1, 131.2, 130.6, 123.8, 122.5, 121.7, 114.6, 112.5, 111.8, 109.5, 108.5, 30.5, 30.4, 30.2, 29.6, 25.7, 25.4, 25.1, 25.0, 14.6, 14.5; IR (CsI): $\nu$=2950 cm⁻¹, 2918, 2855, 1455, 1210, 1035; UV/VIS (CH₂Cl₂): λ=372 (ε=121,000), 383 sh (101,000), 565 (34,000), 608 (28,600), 643 (44,000).

Example 7

Repeating the procedure of Example 6, but substituting 2,7,12,17-tetramethylporphycene; 2,7,12,17-tetrahexylporphycene; 2,7,12,17-tetradecylporphycene, 2,7,12,17-tetraphenylporphycene and 2,7,12,17-tetrabenzylporphycene yields 3-bromo-2,7,12,17-tetramethylporphycene; 3-bromo-2,7,12,17-tetrahexylporphycene; 3-bromo-2,7,12,17-tetradecylporphycene; 3-bromo-2,7,12,17-tetraphenylporphycene and 3-bromo-2,7,12,17-tetrabenzylporphycene.

Example 8

3-Iodo-2,7,12,17-tetrapropylporphycene

To a solution of 50 mg (0.1 mmol) of 2,7,12,17-tetrapropylporphycene in 50 ml of dichloromethane maintained at 0° C. 26 mg (0.1 mmol) of iodine were added. After stirring for 2 min the mixture was shaken with an aqueous KI solution. After drying the organic phase with Na₂SO₄ the solvent was evaporated. The material thus obtained was chromatographed (silicagel; hexane/dichloromethane 4:1) and recrystallized from CCl₄ yielding 45 mg (80%) of the iodo derivative as blue crystals melting between 184° and 186° C.

¹H NMR (300 MHz, CDCl₃): δ=10.37, 9.73, 9.67, 9.56, 9.28, 9.17, 3.96, 2.32, 2.08, 1.34; ¹³C NMR (75.5 MHz, CDCl₃): δ=150.5, 148.9, 147.7, 145.5, 143.6, 142.5, 139.2, 138.3, 138.2, 135.3, 131.9, 130.7, 124.1, 122.9, 121.9, 112.6, 112.0, 109.6, 108.6, 85.9, 32.3, 30.6, 30.5, 30.3, 26.0, 25.5, 25.2, 25.1, 14.7, 14.6, 14.5; IR (CsI): $\nu$=2942 cm⁻¹, 2929, 2858, 1454, 1032, 938; UV/VIS (CH₂Cl₂): λ=373 (ε=140,000), 385 (122,000), 568 (42,500), 609 (33,000), 645 (49,000).

Example 9

9-Nitro-2,7,12,17-tetrapropylporphycene

To a solution of 50 mg (0.1 mmol) of 2,7,12,17-tetrapropylporphycene in 50 ml of acetic acid 360 m (2 mmol) of silver nitrate were added. The reaction mixture was stirred at 60° C. for 15 min. After addition of 50 ml of water the mixture was extracted with dichloromethane. The combined organic phases were dried ($Na_2SO_4$) and the solvent was evaporated. Chromatography of the residue on silicagel with hexane/dichloromethane 2:1 resulted in the isolation of the nitro compound in 85% yield (50 mg) as blue plates (mp>300° C.).

$^1$H NMR (300 MHz, $CDCl_3$): δ=9.95, 9.70, 9.30, 9.26, 9.24, 9.18, 3.98, 3.82, 3.69, 2.94, 2.35, 1.30; $^{13}$C NMR (75.5 MHz, $CDCl_3$): δ=146.7, 146.3, 145.5, 145.1, 144.6, 142.0, 138.4, 138.3, 136.5, 136.4, 136.0, 133.9, 133.4, 125.8, 123.7, 123.0, 122.8, 112.7, 111.1, 105.5, 30.9, 30.2, 30.1, 25.0, 24.9, 24.8, 24.1, 14.5; IR (CsI): ν=2954 $cm^{-1}$, 2924, 2866, 1520, 1347; UV/VIS ($CH_2Cl_2$): λ=373 (ε=76,000), 565 (23,700), 603 (26,100), 635 (30,000).

Example 10

9-Amino-2,7,12,17-tetrapropylporphycene

A solution of 26 mg (0.05 mmol) of 9-nitro-2,7,12,17-tetrapropylporphycene in 25 ml of dichloromethane was mixed with 10 ml of an aqueous 10% sodium hydroxide solution. 2 g (10 mmol) of sodium dithionite were added and the reaction mixture was heated under reflux for 1 hr. After washing with water and drying over $Na_2SO_4$ the solvent was evaporated. The resulting material was purified by chromatography on silicagel (hexane/dichloromethane 2:1) and subsequent recrystallization from hexane/dichloromethane. The amine thus obtained in 50% yield (12 mg) formed blue needles melting at 218°-220° C.

$^1$H NMR (300 MHz, $CDCl_3$): δ=9.34, 8.97, 8.50, 5.48, 5.34 4.83 3.90 3.74 3.57 2.29 1.33 $^{13}$C NMR (75.5 MHz, $CDCl_3$): δ=145.5, 145.1, 143.5, 142.6, 140.8, 140.0, 139.4, 135.6, 133.4, 132.7, 132.6, 131.9, 123.6, 122.7, 121.9, 120.6, 113.5, 107.0, 100.2, 33.9, 30.3, 25.4, 25.0, 24.5, 23.2, 14.6, 14.5; IR (CsI): ν=3377 $cm^{-1}$, 3225, 2953, 2926, 2866, 1619, 1192; UV/VIS ($CH_2Cl_2$): λ=370 (ε=82,300), 400 (60,000), 563 (22,000), 668 (28,000), 703 (14,000).

Example 11

Repeating Example 9 using the corresponding 2,7,12,17-tetramethyl, tetrahexyl, tetraphenyl and tetrabenzyl porphycene compounds yields the corresponding 9-nitro derivatives. Repeating Example 10 using the 9-nitro compounds gives the corresponding 9-amino 2,7,12,17-tetramethyl, tetrahexyl, tetraphenyl and tetrabenzyl porphycenes.

Example 12

9-Acetoxy-2,7,12,17-tetrapropylporphycene 96 mg (0.2 mmol) of 2,7,12,17-tetrapropylporphycene in 30 ml of dry dichloromethane and 15 ml of dry tetrahydrofuran were treated with 600 mg (1.4 mmol) of lead tetraacetate. After heating to reflux for 10 min, the mixture was allowed to cool, quenched with 2 ml of glycol to destroy any lead (IV) present, and washed with water (2×300 ml). The solution was dried with sodium sulphate, evaporated and chromatographed on silica gel (column: 60×3 cm) with chloroform/hexane (1:1). The first fraction contained unchanged starting material (29 mg, 30%). The title compound was obtained in the second fraction, which was recrystallized from ethanol to yield 32 mg (30%) of violet needles (m.p. 174°-175° C.).

$^1$H NMR (300 MHz, $CDCl_3$): δ=9.71, 9.64, 9.40, 9.29, 9.27, 9.23, 3.97, 3.84, 3.65, 3.19, 2.86, 2.40, 1.35; $^{13}$C NMR (75.5 MHz, $CDCl_3$): δ=172.0, 145.6, 144.9, 144.7, 143.1, 140.4, 138.1, 138.0, 134.8, 134.3, 133.3, 124.8, 123.1, 122.9, 122.8, 111.4, 110.4, 106 5, 33.2, 30.4, 30.3, 25.2, 25.1, 24.9, 23.7, 22.1, 14.6, 14.5, 14.4; IR (CsI): ν=1756 $cm^{-1}$, 1464, 1367, 1200; UV/VIS ($CH_2Cl_2$): λ 373 (ε=143,400), 384 sh (94,200), 563 (29,700), 603 (33,300), 634 (32,200).

A third fraction consisted of a mixture of isomeric diacetoxy-2,7,12,17-tetrapropylporphycenes.

Example 13

9-Hydroxy-2,7,12,17-tetrapropylporphycene

To a solution of 27 mg (0.05 mmol) of 9-acetoxy-2,7,12,17-tetrapropylporphycene in 150 ml of dry ether 27 mg (0.5 mmol) of sodium methoxide were added. The reaction mixture wa reacted with 3 ml of dry methanol and stirred at room temperature for five min. The solution was washed with water, dried with sodium sulphate, and evaporated to dryness. The residue was recrystallized from ether/hexane and yielded 22 mg (89%) of the title compound as tiny violet needles decomposing above 250° C. The compound was air sensitive in solution.

$^1$H NMR (300 MHz, [$D_8$]THF): δ=10.47, 9.62, 9.40, 9.25, 9.23, 9.22, 9.21, 4.69, 4.41, 4.03, 3.98, 3.95, 3.90, 2.39, 1.34; $^{13}$C NMR (75.5 MHz, [$D_8$]THF): δ=150.8, 145.9, 144.8, 144.7, 144.5, 144.3, 143.8, 142.5, 135.6, 135.5, 134.9, 134.2, 134.1, 124.5, 123.7, 123.3, 122.2, 113.4, 108.4, 100.4, 34.4, 31.3, 31.0, 26.3, 26.0, 15.0, 14.8; IR (CsI): ν=3436 $cm^{-1}$, 2958, 2930, 2870, 1613, 1563, 1462, 1359, 1184, 810; UV/VIS ($Et_2O$): λ=366 (ε=106,900), 387 sh (66,600), 558 (27,300), 633 (42,800), 679 (20,500).

Example 14

Repeating Examples 12 and 13 using the corresponding 2,7,12,17-tetramethyl, tetrahexyl, tetraphenyl and tetrabenzyl porphycenes yields the corresponding 9-acetoxy porphycene compounds which are hydrolyzed to the corresponding 9-hydroxy 2,7,12,17-tetrasubstituted porphycene derivatives with sodium methoxide.

Example 15

Preparation of porphycenes by McMurry Coupling

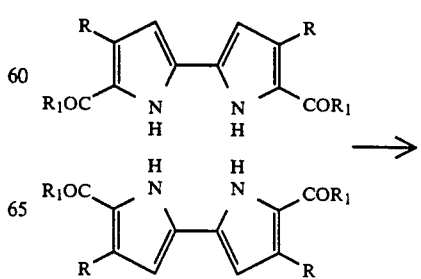

-continued

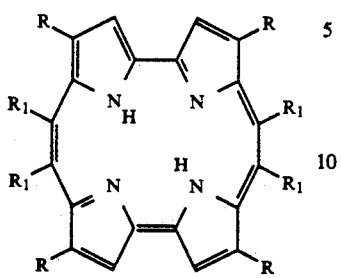

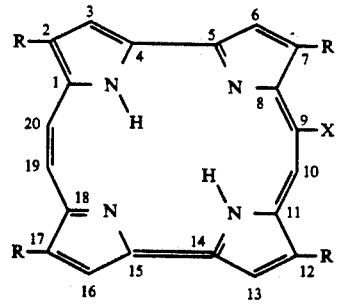

5 mmol of the carbonyl compound (R is H, CH$_3$, C$_3$H$_7$, C$_6$H$_{13}$, C$_6$H$_5$, benzyl; R$_1$ is H) is added to a slurry of titanium(O) reagent (prepared from 50 mmol of titanium tetrachloride and 100 mmol of activated zinc in 400 ml of tetrahydrofuran) and the reaction mixture is heated for ½ to 4 hours (depending on the carbonyl compound). After hydrolysis with aqueous potassium carbonate solution, extraction with dichloromethane and chromatography on silica gel with dichloromethane/hexane (1:1), the porphycene is obtained as the only non-polymeric product in yields from 3-25%.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A pharmaceutical composition, comprising an effective amount of a porphycene having the structure shown below wherein R is C$_{1-6}$alkyl and X is —OCOR$^1$, wherein R$^1$ is C$_{1-6}$alkyl, and a pharmaceutically acceptable carrier.

2. The pharmaceutical composition of claim 1, wherein X is acetoxy.

3. The pharmaceutical composition of claim 1, wherein R is propyl.

4. The pharmaceutical composition of claim 2, wherein R is propyl.

5. The pharmaceutical composition of claim 1, wherein said composition comprises said porphycene within liposomes.

6. The pharmaceutical composition of claim 1, wherein said composition is a dispersion.

7. The pharmaceutical composition of claim 1, wherein said composition is a solution.

8. The pharmaceutical composition of claim 7, wherein said solution is a dimethylsulfoxide solution.

9. The pharmaceutical composition of claim 8, wherein said dimethylsulfoxide solution contains 0-30 wt. % water.

10. A method of treating a tumor sensitive to treatment with photodynamic therapy and accessible to irradiation with light, comprising
topically or parenterally administering to a patient in need thereof an effective amount of the porphycene-containing pharmaceutical composition of claim 1, and irradiating said tumor with an effective amount of light having a wavelength which can be absorbed by said porphycene and generate singlet oxygen.

11. The method of claim 10, wherein X is acetoxy.

12. The method of claim 10, wherein R is propyl.

13. The method of claim 11, wherein R is propyl.

14. The method of claim 10, wherein said pharmaceutical composition comprises said porphycene within liposomes.

15. The method of claim 10, wherein said pharmaceutical composition is a dispersion.

16. The method of claim 10, wherein said pharmaceutical composition is a solution.

17. The method of claim 16, wherein said solution is a dimethylsulfoxide solution.

18. The method of claim 17, wherein said dimethylsulfoxide solution contains 0-30 wt. % water.

19. The method of claim 10, wherein said light has a wavelength from about 600 to 950 nm.

* * * * *

UNITED STATES PATENT AND TRADEMARK OFFICE
CERTIFICATE OF CORRECTION

Page 1 of 2

PATENT NO. : 5,244,671

DATED : September 14, 1993

INVENTOR(S) : Emanuel Vogel, et. al.

It is certified that error appears in the above-indentified patent and that said Letters Patent is hereby corrected as shown below:

Title page, item [56], col. 2, line 1, change "Biomimentic" to --Biomimetic--, and change "Octabinylo-" to --Octavinylo- --;

lines 2 and 5, change "Knubel" to --Knübel--;

line 4, change "Octabinylogen" to --Octavinylogen--;

line 14, change "26" to --26 $\pi$--;

line 20, change "22" to --22 $\pi$--;

line 27, change "-Carotene" to --$\beta$-Carotene--;

line 30, change "Phtoradia-" to --Photoradia- --.

Column 1, line 16, change "case" to --cases--.

UNITED STATES PATENT AND TRADEMARK OFFICE
CERTIFICATE OF CORRECTION

PATENT NO. : 5,244,671
DATED : September 14, 1993
INVENTOR(S) : Emanuel Vogel, et. al.

It is certified that error appears in the above-indentified patent and that said Letters Patent is hereby corrected as shown below:

Column 5, lines 39 and 40, change " Hydroxylation $\longrightarrow$ " to -- $\underset{\longrightarrow}{Pb(OAc)_4}$ P-OAc $\longrightarrow$ --;

line 58, change "hydroxide" to --methoxide--.

Signed and Sealed this

Twenty-first Day of November, 1995

Attest:

BRUCE LEHMAN

*Attesting Officer*    Commissioner of Patents and Trademarks